United States Patent [19]
Thebrin et al.

[11] Patent Number: 6,083,347
[45] Date of Patent: Jul. 4, 2000

[54] ABSORBENT MATERIAL AND PRODUCTION THEREOF

[75] Inventors: Ingemar Thebrin; Svante Wåhlèn, both of Stenungsund; Erik Lindgren, Bohus; Kerstin Malmborg, Hjälteby, all of Sweden

[73] Assignee: Eka Chemicals AB, Bohus, Sweden

[21] Appl. No.: 08/823,444

[22] Filed: Mar. 24, 1997

Related U.S. Application Data

[60] Provisional application No. 60/014,607, Apr. 2, 1996.

[30] Foreign Application Priority Data

Mar. 25, 1996 [SE] Sweden ................................ 9601136

[51] Int. Cl.$^7$ .................................................. D21H 17/00
[52] U.S. Cl. ................................... 162/181.1; 162/181.9; 162/184
[58] Field of Search ..................................... 442/412, 417; 162/181.1, 181.9, 184; 264/641

[56] References Cited

U.S. PATENT DOCUMENTS

| | | | |
|---|---|---|---|
| 4,826,497 | 5/1989 | Marcus et al. ........................... | 604/359 |
| 5,429,628 | 7/1995 | Trinh et al. ............................... | 604/359 |
| 5,516,569 | 5/1996 | Veith et al. ............................... | 428/68 |
| 5,571,604 | 11/1996 | Sprang et al. ........................... | 428/212 |
| 5,662,876 | 9/1997 | Tour et al. ............................... | 423/445 |

FOREIGN PATENT DOCUMENTS

| | | | |
|---|---|---|---|
| 0 540 076 | 5/1993 | European Pat. Off. | ....... D21H 17/68 |
| WO 91/11977 | 8/1991 | WIPO | ............................. A61F 13/15 |

OTHER PUBLICATIONS

PCT International Search Report, Jul. 8, 1997.

*Primary Examiner*—Elizabeth M. Cole
*Attorney, Agent, or Firm*—Ralph J. Mancini; Lainie E. Parker

[57] ABSTRACT

The present method generally relates to a method for production of absorbent material having improved sorptive capacity, which material comprises cellulosic fibres, wherein said method comprises treating said fibres, in the presence of water, with a hydrophobic substance having a specific surface area of at least 50 m$^2$/g, wherein the treatment comprises contacting said substance and said fibres together when the fibres have a dry content of at least 20%.

10 Claims, No Drawings

ABSORBENT MATERIAL AND PRODUCTION THEREOF

This present application claims priority of Swedish patent application no. 9601136-6 filed on Mar. 25, 1996 and benefit of U.S. provisional application Ser. No. 60/014,607 filed Apr. 2, 1996 under 35 U.S.C. §119.

FIELD OF INVENTION

The present invention relates to a method for production of absorbent material having improved sorptive capacity, to absorbent material obtainable by such a method, and to absorbent articles comprising such material. Furthermore, the invention relates to a process for production of an absorbent structure comprising such absorbent material.

BACKGROUND OF THE INVENTION

In the present context the concept of "sorptive capacity" aims at the rate by which the absorbent material takes up liquids such as water or aqueous solutions, including body fluids such as urine, blood and menstrual fluids, or to the liquid-retaining capacity of the absorbent material, or to both of these characteristics. The sorptive mechanism may be adsorption or absorption, or a combination thereof.

In the present context the concept of "absorbent material" is intended to comprise, among other things, any paper or paper-like structure, that consists mainly of cellulosic fibres, the principal use of which is to absorb liquids such as water or aqueous solutions, including body fluids such as urine, blood and menstrual fluids. Exemplary of such papers are hygienic paper and paper to be impregnated with thermosetting resins for production of decorative laminates As stated in Ullmann's encyclopedia of industrial chemistry, Vol. A 18, page 663, 1991, hereby incorporated by reference, the term hygienic paper encompasses cellulose wadding, soft tissue, and crepe paper, all useful within the household or sanitary fields. It is well known that the rate of liquid uptake and liquid-holding capacity of hygienic paper are important when used in these fields. This is particularly valid with regard to absorbent articles such as catamenial devices (e.g. sanitary napkins, pantiliners, tampons etc.), diapers, bandages, adult incontinence garments, and the like; good liquid uptake and liquid-holding capacity are obvious prerequisites for the function of such articles. However, when used, an article of this kind is constantly subjected to pressure imposed by the weight and the movements of the bearer, and thus it is important that the liquid-holding capacity is high enough to retain the absorbed liquid also under pressure. Furthermore, in order to give good comfort to the bearer, the article should provide a feeling of dryness, meaning that any rewetting from the article to the skin of the bearer should by avoided, raising the requirements with regard to liquid-holding capacity even higher. Conventionally, certain polymeric materials forming hydrogels in contact with water, known as "superabsorbents", have been utilised to enhance the sorptive capacity of such articles; however, although this capacity of the article is enhanced, as the liquid is bound to superabsorbent particles, the sorptive capacity of the cellulosic fibres making up the hygienic paper itself is not in fact enhanced by the use of such superabsorbents.

Another field in which the sorptive capacity of cellulosic material is important is that of laminates, particularly so-called decorative laminates, such as described in U.S. Pat. No. 3,373,071. Such laminates conventionally comprise at least three layers: a wear surface layer, a print or pattern layer beneath the wear surface layer, and a core layer supporting the wear surface and print layers. All layers consist of paper sheet impregnated with thermosetting resin. The wear surface layer usually consists of translucent paper impregnated with melamine resin. The impregnation is carried out by submerging the paper in an aqueous solution of the resin. Obviously the sorptive capacity of the paper is a critical parameter for the efficiency of the impregnation.

The problem to be solved by the present invention is thus to provide a method for production of absorbent material having improved sorptive capacity.

SUMMARY OF THE INVENTION

The present method generally relates to a method for production of absorbent material having improved sorptive capacity, which material comprises cellulosic fibres, wherein said method comprises treating said fibres, in the presence of water, with a hydrophobic substance having a specific surface area of at least 50 $m^2/g$, wherein the treatment comprises contacting said substance and said fibres together when the fibres have a dry content of at least 20%.

DETAILED DESCRIPTION OF THE INVENTION

This problems of the prior art are solved by the method defined by the appended claims. More specifically, the present invention relates to a method for production of absorbent material having improved sorptive capacity, which material comprises cellulosic fibres, in which the fibres are treated, in the presence of water, with a hydrophobic substance having a specific surface area of at least 50 $m^2/g$, by bringing the substance and the fibres together when the fibres have a dry content of at least 20%.

It is believed that the reason behind the improved sorption characteristics imposed by the hydrophobic substances of the stated kind may be that the substances absorbate surface active substances naturally occurring in or on the cellulosic fibres To "treat" the fibres with a hydrophobic substance means that particles of the substance are brought into the proximity of, or in contact with the fibres when the dry matter content of the fibres is at least about 20%, suitably at least about 25%, and most preferably at least about 30%. This means that the present method may be carried out in a process for production of absorbent paper once the drainage or dewatering of the web is completed. In this application "web" also comprises the concept of "sheet". Preferably, the particles are kept in the proximity of, or in contact with, the fibres for at least about 10 seconds, suitably at least about 5 seconds, and particularly at least about 2 seconds.

The specific surface area of the hydrophobic substance particles, determined according to standard method DIN 66131 modified as described below, is at least about 50 $m^2/g$, preferably at least about 100 $m^2/g$, and most preferably at least about 200 $m^2/g$. For activated carbon the specific surface area is about 1000 $m^2/g$, for zeolite of type ZSM-5 and type A it is about 500 $m^2/g$, whereas zeolite X and Y both have a specific surface areas of about 800 $m^2/g$.

The hydrophobic substance may be any substance that is substantially insoluble in water, preferably having a solubility not higher than about 1 g/100 g of water, suitably not higher than about 0.1 g/100 g of water, as long as it has a specific surface area as indicated above. Exemplary of useful hydrophobic substances are activated carbon, hydrophobic zeolites, and polytetrafluoroethylene (i.e. Teflon). The substances are preferably porous. In a particularly preferred embodiment the hydrophobic substance is activated carbon or a zeolite having a hydrophobicity of below about 0.99 percent, preferably below about 0.90 percent, and suitably below about 0,70 percent by weight residual butanol as determined by the Residual Butanol Test described below. Especially preferred zeolites are those having a molar relation $SiO_2/Al_2O_3$ of about 5.

Although the hydrophobic substance may be brought to the fibres in a dry as well as a wet state, it is preferred that the substance is comprised in an aqueous mixture, usually as a dispersion or a slurry. The mixture is applied on the web, conveniently by spraying or showering. The amount of substance added is suitably about 0.1–10 kg/metric ton dry pulp, preferably about 0.5–5 kg/ton. Optionally the treatment may be carried out by pouring the substance, preferably comprised in an aqueous mixture, onto the web, or by submerging the web into such a mixture.

The treatment may be carried out in the presence of a retention agent to ensure that a sufficient amount of the substance particles are kept in contact with, or in the proximity of the fibres long enough to give the desired effect. Exemplary of preferred retention agents are polysaccharides, such as starch, cellulose derivatives, xanthan gum and guar gum, and synthetically produced homopolymers, such as polyacryl amide (PAM), polyamide amine (PAA), polydiallyl dimethyl ammonium chloride (polyDADMAC), polyethylene imine (PEI) and polyethylene oxide (PEO), or copolymers thereof.

Although the substance may remain in the absorbent paper after the treatment, this is not considered to be essential to the invention. In fact, even if less than about 65%, say less than 30%, or even as little as about 1% of the substance used in the treatment is present in the absorbent paper after the treatment, the sorption effect is quite noticeably enhanced when compared to untreated paper. In some instances it may however be advantageous to let a substantial amount of substance remain in the paper, for instance when the substance is a hydrophobic zeolite providing such odour eliminating characteristics to absorbent articles, e.g. diapers and catamenial devices, as disclosed in U.S. Pat. No. 4,826,497 and WO 91/11977; it should, however, be noted that in those documents the zeolite is not used for treatment of the fibres in the presence of water.

The present invention also relates to absorbent material obtainable by the present method, specifically hygienic paper, and to absorbent articles such as diapers, sanitary napkins, pantiliners, tampons, bandages, adult incontinence garments, toilet paper, handkerchiefs, kitchen towels, hand towels, face towels, serviettes, and similar articles comprising such paper. Furthermore, the invention relates to a process for production of an absorbent structure comprising such absorbent material.

In another embodiment the absorbent material is paper to be impregnated with thermosetting resin and used in the production of laminates, particularly as overlays in decorative laminates.

Absorbent material, e.g. hygienic paper, may be produced by any suitable paper-making process. Soft tissue and cellulose wadding qualities are usually manufactured by means of a so-called Yankee machine, i.e. a paper machine in which the drying is achieved substantially on a Yankee cylinder or Yankee dryer, which is a drying cylinder with a large diameter and a polished surface which is largely responsible for the drying of the paper web. Usually the wet web is adhered to the Yankee cylinder at 20–35% dryness with one or two pressure rolls; in this context, the present invention may be carried out by means of spray showers situated before the first pressure roll.

The fibres making up the pulp sheet are usually obtained by disintegrating wood, conventionally in the form of chips, into fibres or bundles of fibres; in the present context the concept of "bundles of fibres" is regarded to be equivalent to the concept of "fibres". The separated fibres may be obtained by means of any pulp-making method known to a skilled person, e.g. by a method for production of mechanical pulp (MP), stone groundwood pulp (SGW), pressure groundwood pulp (PGW), refiner mechanical pulp (RMP), thermo-mechanical pulp (TMP), chemi-mechanical pulp (CMP), or chemi-thermomechanical pulp (CTMP), although the preferred pulps are chemical pulps such as, for instance, sulphate and sulphite pulps. However, the cellulosic fibres may also be cotton fibres. Another plausible source of fibres is recycled fibres from wastepaper.

The present invention is illustrated in more detail below by means of examples. Unless otherwise stated the parts and percentages below are given by weight. In the Examples below, the absorbent material obtained is tested with respect to rewetting and/or with respect to the uptake rate. The test method for determination of the uptake rate was SCAN-P 61-87, in which test a sample consisting of a bundle of six tissue sheets is placed in an apparatus especially designed for the test method, which is equipped with electrodes for detection of penetrating water in the machine direction, in the cross direction, and in the direction perpendicular to the surface of the tissue, respectively. The time elapsing from application of a certain amount of water on the tissue until the electrodes detect the penetration is determined for the respective directions. The shorter time required to penetrate the material, the higher is the uptake rate of the material.

EXAMPLE 1–2

Tissue made from a pulp composition containing 40% sulphate pulp of eucalyptus wood, 36% sulphate pulp of pine, and 24% sulphite pulp of spruce was used in this Example. The basis weight of the tissue was 18.6 g/m$^2$. An aqueous solution containing 0.2% of a zeolite was sprayed onto one sample; said zeolite was of Y type and had a hydrophobicity of 0.28 percent by weight residual butanol as determined by the Residual Butanol Test, and a $SiO_2/Al2O_3$ ratio of 29. The specific surface area was measured to be about 800 m$^2$/g by a method based on DIN 66131 (the so-called BET method), in which the area is determined at one spot at a relative pressure $P/P_0$ of 0.03. The amount of zeolite added to the sample corresponded to 3 kg zeolite/ metric ton of dry tissue. The tissue sample was allowed to dry and was then tested for determination of the uptake rates. Example 1 is a comparison example with no zeolite added. The results are set forth in Table I below.

TABLE I

| Ex | Uptake rate in machine direction, s | Uptake rate in cross direction, s | Uptake rate in direction perpendicular to tissue surface, s |
|---|---|---|---|
| 1 | 2.88 | 0.81 | 0.06 |
| 2 | 2.42 | 0.68 | 0.04 |

Tissue treated according to the present invention thus evidently has a faster uptake rate than untreated tissue.

We claim:

1. A method for production of absorbent material having improved sorptive capacity, for water or aqueous solutions, which material comprises cellulosic fibers wherein said method comprises treating said fibers in the presence of water, with a hydrophobic substance having a specific surface area of at least 50 $m^2/g$, wherein the treatment comprises contacting said substance and said fibers together when the fibers have a dry content of at least 20%.

2. The method of claim 1, wherein a web of said absorbant material is formed by draining an aqueous suspension of cellulosic fibres and then pressing and/or drying the web, and wherein the web is treated with the substance after the draining.

3. The method of claim 1 wherein the fibres are sprayed or showered with a mixture comprising the substance and water.

4. The method of claim 1 wherein the substance is activated carbon or a zeolite having a hydrophobicity of below about 0.99 percent by weight residual butanol as determined by the Residual Butanol Test.

5. A process for the production of an absorbent structure comprising absorbent material, which contains cellulosic fibers, which structure has improved sorptive capacity for water or aqueous solutions, wherein said process comprises treating said cellulose fibers, in the presence of water, with a hydrophobic substance having a specific surface area of at least 50 $m^2/g$, wherein said treatment comprises bringing the substance and the fibers together at a dry content of the fibers of at least 20%.

6. A method for production of absorbent material having improved sorptive capacity for water or aqueous solutions which material comprises cellulosic fibers, wherein said method comprises treating said fibers, in the presence of water, with a hydrophobic zeolite having a specific surface area of at least 50 $m^2/g$, wherein the treatment comprises contacting said zeolite and said fibers together when the fibers have a dry content of at least 20%.

7. The method of claim 6, wherein the zeolite has a molar ratio of $SiO_2/Al_2O_3$ of about 5.

8. The method of claim 6, wherein the zeolite has a hydrophobicity below about 0.90 percent by weight residual butanol.

9. The method of claim 6, wherein the zeolite has a specific surface area of at least about 200 $m^2/gram$.

10. The method of claim 6, herein the dry content of the fibers is at least about 30%.

* * * * *